US00PP28117P2

(12) United States Plant Patent
Heuger

(10) Patent No.: US PP28,117 P2
(45) Date of Patent: Jun. 13, 2017

(54) ***ARGYRANTHEMUM* PLANT NAMED 'SUN 410'**

(50) Latin Name: *Argyranthemum frutescens*
Varietal Denomination: SUN 410

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 14/998,600

(22) Filed: Jan. 23, 2016

(51) Int. Cl.
*A01H 5/02* (2006.01)

(52) U.S. Cl.
USPC ..... Plt./406

(58) Field of Classification Search
USPC ..... Plt./406
See application file for complete search history.

(56) References Cited

PUBLICATIONS

PLUTO Plant Variety Database Jan. 5, 2017. p. 1.*

* cited by examiner

*Primary Examiner* — Annette Para
(74) *Attorney, Agent, or Firm* — C. A. Whealy

(57) ABSTRACT

A new and distinct cultivar of *Argyranthemum* plant named 'SUN 410', characterized by its uniformly mounded plant habit; freely branching habit; freely flowering habit; single-type inflorescences with red purple-colored ray florets; and good garden performance.

2 Drawing Sheets

Botanical designation: *Argyranthemum frutescens.*
Cultivar denomination: 'SUN 410'.

BACKGROUND OF THE INVENTION

The present invention relates to a new and distinct cultivar of *Argyranthemum* plant, botanically known as *Argyranthemum frutescens* and hereinafter referred to by the cultivar name 'SUN 410'.

The objective of the breeding program is to create new *Argyranthemum* plants with attractive ray and disc floret colors and good garden performance and pest resistance.

The new *Argyranthemum* plant originated from a cross-pollination made by the Inventor in August, 2012 in Glandorf, Germany of two unnamed seedling selections of *Argyranthemum frutescens*, not patented. The new *Argyranthemum* plant was discovered and selected by the Inventor as a single flowering plant from within the progeny of the stated cross-pollination in a controlled greenhouse environment in Glandorf, Germany in July, 2013.

Asexual reproduction of the new *Argyranthemum* plant by vegetative tip cuttings was first conducted in Glandorf, Germany in February, 2014. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new

*Argyranthemum* plant. These characteristics in combination distinguish 'SUN 410' as a new and distinct *Argyranthemum* plant:

1. Uniformly mounded plant habit.
2. Freely branching habit.
3. Freely flowering habit.
4. Single-type inflorescences with red purple-colored ray florets.
5. Good garden performance.

Plants of the new *Argyranthemum* differ from plants of the parent selections primarily in uniformity as plants of the new *Argyranthemum* are more uniformly mounding than plants of the parent selections.

Plants of the new *Argyranthemum* can be compared to plants of *Argyranthemum frutescens* 'SUN 180', not patented. In side-by-side comparisons conducted in Glandorf, Germany, plants of the new *Argyranthemum* differed primarily from plants of 'SUN 180' in ray floret color as plants of 'SUN 180' have pink-colored ray florets.

BRIEF DESCRIPTION OF THE PHOTOGRAPHS

The accompanying photographs illustrate the overall appearance of the new *Argyranthemum* showing the colors as true as it is reasonably possible to obtain in colored reproductions of this type. Colors in the photographs may differ slightly from the color values cited in the detailed botanical description which accurately describe the colors of the new *Argyranthemum* plant.

The photograph on the first sheet comprises a side perspective view of a typical flowering plant of 'SUN 410' grown in a container.

The photograph on the second sheet is a close-up view of a typical flowering plant of 'SUN 410'.

DETAILED BOTANICAL DESCRIPTION

The aforementioned photographs and following observations and measurements describe plants grown during the spring and early summer in 9-cm containers in a glass-covered greenhouse in Glandorf, Germany and under cultural practices typical of commercial potted *Argyranthemum* production. During the production of the plants, day temperatures ranged from 14° C. to 28° C., night temperatures ranged from 10° C. to 18° C. and light levels ranged from 25 klux to 90 klux. Plants were pinched one time five weeks after planting and were 2.5 months old when the photographs and description were taken. In the following description, color references are made to The Royal Horticultural Society Colour Chart, 2007 Edition, except where general terms of ordinary dictionary significance are used.

Botanical classification: *Argyranthemum frutescens* 'SUN 410'.

Parentage:

*Female, or seed, parent*.—Unnamed seedling selection of *Argyranthemum frutescens*, not patented.

*Male, or pollen, parent*.—Unnamed seedling selection of *Argyranthemum frutescens*, not patented.

Propagation:

*Type*.—Terminal cuttings.

*Time to initiate roots, summer*.—About 8 to 10 days at temperatures about 18° C. to 24° C.

*Time to initiate roots, winter*.—About 10 to 15 days at temperatures about 14° C. to 18° C.

*Time to produce a rooted young plant, summer*.—About 14 to 16 days at temperatures about 18° C. to 24° C.

*Time to produce a rooted young plant, winter*.—About 16 to 20 days at temperatures about 14° C. to 18° C.

*Root description*.—Fine to medium in thickness, fibrous; typically white in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial; uniformly mounding plant habit; upright to broadly spreading form; overall shape, roughly flattened globular; moderately vigorous growth habit.

*Branching habit*.—Freely branching growth habit with about ten lateral branches developing per plant; pinching enhances lateral branch development.

*Plant height*.—About 14.9 cm.

*Plant width*.—About 23.3 cm.

*Lateral branches*.—Length: About 8.2 cm. Diameter: About 3.5 mm. Internode length: About 1.1 cm. Strength: Strong; young stems, flexible. Texture: Smooth, glabrous. Luster: Moderately glossy. Color: Close to 138B to 138C; axial stripes, close to 146A to 146B.

Leaf description:

*Arrangement*.—Alternate, simple; sessile.

*Length*.—About 6.9 cm.

*Width*.—About 4.2 cm.

*Shape*.—Pinnatisect; in outline, obovate.

*Apex*.—Acute.

*Base*.—Cuneate.

*Margin*.—Deeply incised.

*Sinuses*.—Slightly convergent.

*Texture, upper and lower surfaces*.—Smooth, glabrous; leathery.

*Luster, upper surface*.—Matte.

*Luster, lower surface*.—Slightly glossy.

*Venation*.—Pinnate.

*Color*.—Developing leaves, upper surface: Close to 141B. Developing leaves, lower surface: Close to 143B. Fully expanded leaves, upper surface: Close to N137A; venation, close to 138A to 138B. Fully expanded leaves, lower surface: Close to between 137C and 138A; venation, close to 138A.

Inflorescence description:

*Inflorescence form and arrangement*.—Single-type terminal and axillary inflorescences held above and beyond the foliar plane on strong peduncles; ray and disc florets arranged acropetally on a receptacle; inflorescences face mostly upright to slightly outwardly.

*Flowering habit*.—Freely flowering habit with about 200 inflorescences developing per plant during the flowering season.

*Flowering season*.—Plants flower from spring to late summer in Germany; flowering continuous during this period.

*Inflorescence longevity*.—Inflorescences last about two to three weeks on the plant; inflorescences not persistent.

*Fragrance*.—Moderately faintly fragrant.

*Inflorescence buds*.—Height: About 5 mm. Diameter: About 7 mm. Shape: Flattened globular. Color: Towards the base, close to 143C; towards the apex, close to between 200A and 200B; towards the margins, close to 199C.

*Inflorescence size*.—Diameter: About 4.4 cm. Depth (height): About 1.4 cm. Diameter of disc: About 1.4 cm. Receptacle diameter: About 5 mm. Receptacle height: About 3 mm.

*Ray florets*.—Quantity per inflorescence and arrangement: About 30 arranged in about two whorls. Length: About 2 cm. Width: About 5.5 mm. Shape: Elliptic to narrowly ovate. Apex: Retuse to shallowly praemorse. Base: Attenuate. Margin: Entire. Texture, upper surface: Smooth, glabrous; velvety. Texture, lower surface: Glabrous; slightly carinate. Luster, upper surface: Matte. Luster, lower surface: Moderately glossy. Color: When opening, upper surface: Close to NN155C; towards the apex, close to 72B. When opening, lower surface: Close to 58A. Fully opened, upper surface: Close to between 53A and 59B; with development, color becoming closer to between 59B to 59C. Fully opened, lower surface: Close to N74D; color does not change with development.

*Disc florets*.—Quantity per inflorescence and arrangement: About 175 spirally arranged at center of receptacle. Length: About 6 mm. Diameter, apex: About 2 mm. Diameter, base: About 0.5 mm. Shape: Tubular with five free apical lobes. Apex: Acute. Texture, inner and outer surfaces: Smooth, glabrous. Luster, inner surface: Glossy. Luster, outer surface: Matte. Color, immature, inner and outer surfaces: Apex: Close to 175A. Mid-section: Close to 22A. Base: Close to 145D. Color, mature, inner and outer surfaces: Apex: Close to 12A; tipped with close to 175A. Mid-section: Close to 150B. Base: Close to 150D.

*Phyllaries*.—Quantity per inflorescence and arrangement: About 20 arranged in two whorls. Length: About 4 mm. Width: About 2.5 mm. Shape: Ovate.

Apex: Praemorse. Base: Broadly cuneate. Margin: Entire. Texture, upper and lower surfaces: Smooth, glabrous; edges, papery. Luster, upper surface: Glossy. Luster, lower surface: Matte. Color, upper surface: Close to 144C; margins and papery edges, close to 199C. Color, lower surface: Close to 144A; margins and papery edges, close to 199C to 199D.

*Peduncles*.—Length, terminal peduncle: About 1.4 cm. Length, fourth peduncle: About 4 cm. Diameter: About 1.5 mm. Angle: Terminal peduncle, erect; lateral peduncles, about 45° from branch axis. Strength: Strong. Texture: Slightly ribbed, glabrous. Luster: Slightly glossy. Color: Close to 138A to 138B.

*Reproductive organs*.—Androecium: Present on disc florets only. Filament length: About 2.5 mm. Anther length: About 1 mm. Anther shape: Lanceolate; basifixed. Anther color: Close to 6A. Pollen amount: Moderately high. Pollen color: Close to 17B. Gynoecium: Present on both ray and disc florets. Pistil length: About 4 mm. Stigma shape: Decurrent. Stigma color: Close to 3A. Style length: About 3 mm. Style color: Close to 145A. Ovary color: Close to 145D.

*Seeds and fruits*.—Seed and fruit production has not been observed on plants of the new *Argyranthemum*.

Disease & pest resistance: Plants of the new *Argyranthemum* have not been shown to be resistant to pathogens and pests common to *Argyranthemum* plants.

Garden performance: Plants of the new *Argyranthemum* have been observed to have good garden performance and to tolerate rain, wind, high temperatures about 40° C. and to be hardy to USDA Hardiness Zone 9.

It is claimed:

1. A new and distinct *Argyranthemum* plant named 'SUN 410' as illustrated and described.

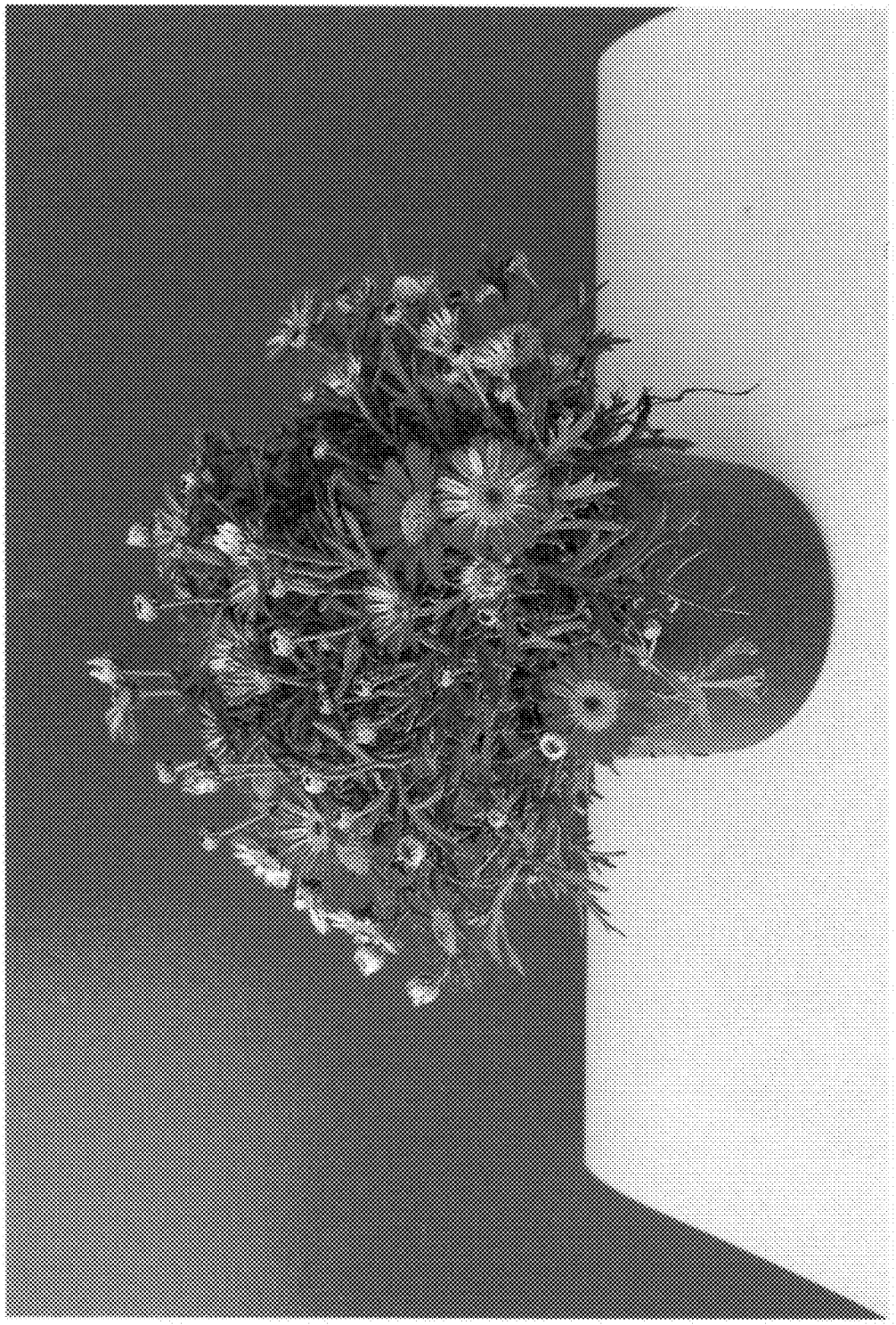

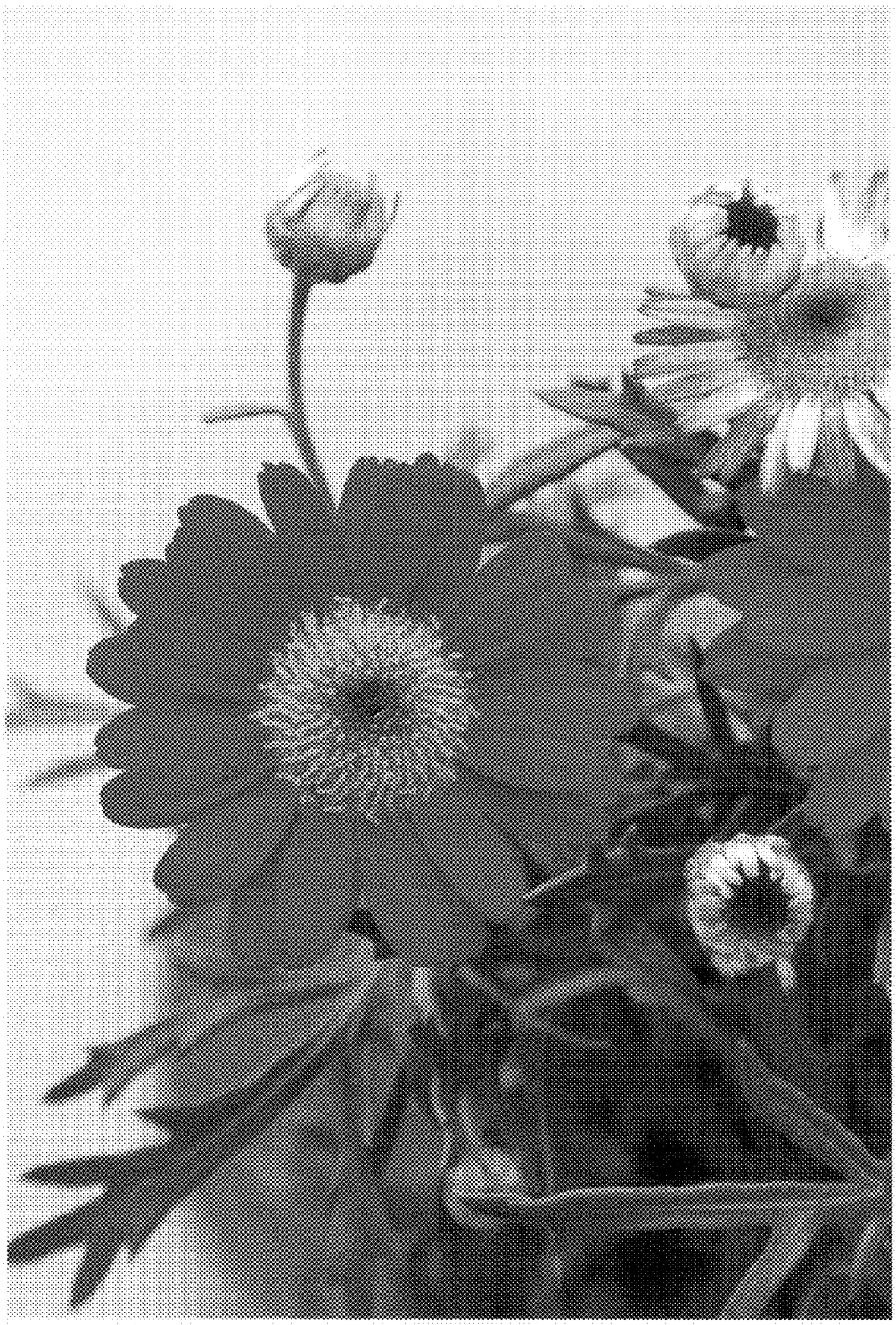

* * * * *